US008529502B2

(12) United States Patent
Radmer

(10) Patent No.: US 8,529,502 B2
(45) Date of Patent: Sep. 10, 2013

(54) TRANSFER SYSTEM FOR FORMING A DRUG SOLUTION FROM A LYOPHILIZED DRUG

(75) Inventor: Bo Radmer, Hillerød (DK)

(73) Assignee: Novo Nordisk Healthcare AG, Zurich (CH)

(*) Notice: Subject to any disclaimer, the term of this patent is extended or adjusted under 35 U.S.C. 154(b) by 1010 days.

(21) Appl. No.: 12/298,082

(22) PCT Filed: Apr. 23, 2007

(86) PCT No.: PCT/EP2007/053935
§ 371 (c)(1),
(2), (4) Date: Nov. 19, 2008

(87) PCT Pub. No.: WO2007/122209
PCT Pub. Date: Nov. 1, 2007

(65) Prior Publication Data
US 2009/0099547 A1 Apr. 16, 2009

Related U.S. Application Data

(60) Provisional application No. 60/796,413, filed on May 1, 2006.

(30) Foreign Application Priority Data

Apr. 24, 2006 (DK) .................................. 2006 00576

(51) Int. Cl.
A61M 37/00 (2006.01)
(52) U.S. Cl.
USPC ................... 604/82; 604/83; 604/84; 604/85; 604/92

(58) Field of Classification Search
USPC ..................... 604/82–92, 207–211
See application file for complete search history.

(56) References Cited

U.S. PATENT DOCUMENTS

| 4,543,101 | A | * | 9/1985 | Crouch | 604/411 |
| 5,466,220 | A | * | 11/1995 | Brenneman | 604/87 |
| 6,364,865 | B1 | | 4/2002 | Lavi et al. | |
| 6,475,183 | B1 | * | 11/2002 | Epstein et al. | 604/82 |
| 2007/0106244 | A1 | | 5/2007 | Mosler et al. | |

(Continued)

FOREIGN PATENT DOCUMENTS

| FR | 2850015 | 7/2004 |
| JP | H11/500931 A | 1/1999 |

(Continued)

OTHER PUBLICATIONS

Search Report issued in connection with counterpart PCT Application No. PCT/EP2007/053935, mailed Jul. 27, 2007.

Primary Examiner — Kevin C Sirmons
Assistant Examiner — Edelmira Bosques
(74) Attorney, Agent, or Firm — Wesley A. Nicolas; Marc A. Began; Reza Green

(57) ABSTRACT

A transfer system (100, 100', 100") adapted to allow first contents of a first container (20) and second contents of a second container (30) to mix to form a material. The mixed material is retrieved to a syringe (40). The transfer system (100, 100', 100") comprises first (17) and second (18) flow control members for controlling fluid flow between the containers (20, 30) and the syringe (40). The invention further relates to a drug mixing kit comprising a container unit containing first and second containers, and a transfer unit comprising ports for receiving the containers and a syringe and a number of flow channels. The container unit and the transfer unit are adapted to be coupled together to form a drug mixing kit.

2 Claims, 13 Drawing Sheets

(56) References Cited

U.S. PATENT DOCUMENTS

2007/0244458 A1 * 10/2007 Fangrow ............... 604/411
2008/0009790 A1    1/2008 Delay

FOREIGN PATENT DOCUMENTS

| JP | 2004/524082 A | 8/2004 |
| JP | 2004/529739 A | 9/2004 |
| WO | WO 93/11709 | 6/1993 |
| WO | WO 94/06690 | 3/1994 |
| WO | WO 95/31955 | 11/1995 |
| WO | WO 01/47571 | 7/2001 |
| WO | WO 2005/120431 | 12/2005 |

* cited by examiner

TRANSFER SYSTEM FOR FORMING A DRUG SOLUTION FROM A LYOPHILIZED DRUG

CROSS-REFERENCE TO RELATED APPLICATIONS

This application is a 35 U.S.C. §371 national stage application of International Patent Application PCT/EP2007/053935 (published as WO 2007/122209), filed Apr. 23, 2007, which claimed priority of Danish Patent Application PA 2006 00576, filed Apr. 24, 2006; this application further claims priority under 35 U.S.C. § 119 of U.S. Provisional Application 60/796,413, filed May 1, 2006.

The present invention relates to the preparation and administration of a product and, more particularly, to the injection of the same into a living organism, for example, a human body.

BACKGROUND OF THE INVENTION

Previously, various devices have been developed for the percutaneous delivery of medications into living organisms including syringes in which a liquid is delivered from a chamber using pressure asserted by a manual plunger through a needle inserted under the skin.

Additionally, it is well known in the art that the storage life of certain injectable substances such as glucagon, used to dissolve blood clots, is increased when the substance is stored in a powdered or lyophilized state, for example. These lyophilized substances (i.e., drugs or compounds) are presently used for injection of materials that would otherwise be unstable. Lyophilization, for example, is the rapid freezing of a material at a very low temperature followed by rapid dehydration by sublimation in a high vacuum. The resulting lyophilized compound is typically stored in a glass vial or cartridge which is closed by a cap, such as a rubber stopper or septum.

It is necessary to reconstitute the powdered or solid material, such as a lyophilized compound, prior to administration. This is accomplished by mixing the solid compound with a suitable diluent or liquid. Reconstitution typically involves the use of a syringe with a needle to withdraw the diluent from a separate vial and inject it into the vial containing the compound. The compound is then thoroughly mixed, typically by shaking the vial by hand, and a separate syringe with a needle withdraws the desired amount to be injected into the patient. Because two separate containers are used, the person reconstituting the compound must be certain to mix the correct amounts such that a proper concentration of the mixture results. When a syringe is used to mix the diluent and drug, the exact volume of diluent to drug ratio is difficult to obtain. Thus, precise concentration levels of administered drug may be compromised.

Moreover, because the diluent and compound are in separate, sterilized containers, the manual withdrawal of diluent via a syringe and reinjection of the same into the container containing the solid material such as a powdered or lyophilized drug may compromise sterility, and safety due to the use of a syringe.

Because of increased use of powdered compounds or lyophilized drugs, for example, it is desirable to provide both professional and non-professional personnel with a reconstituted drug delivery system. It is desirable to have a simple, reliable system that facilitates preparation and safe delivery of an accurate dosage of a reconstituted compound. In addition, it is desirable to provide a system that reconstitutes a lyophilized drug while maintaining sterility throughout the process. Also, it is desirable to provide improvements in the percutaneous delivery of medication generally, which provide for safe, effective administration by the user.

U.S. Pat. No. 6,364,865 discloses various different embodiments of medication delivery systems and transfer systems for forming a solution from constituents from a set of vials respectively containing a lyophilized compound and a diluent.

Sometimes a desired dose of a drug solution is larger than the amount corresponding to the drug contained in a single set of vials. In this case the total dose must be composed using lyophilized drug from two or more vial sets, the number of vial sets corresponding to the desired dose. This may, e.g., be done by sequentially applying a solvent liquid to each of the vials and retrieving the reconstituted drug to one common reservoir or syringe. When the drug of all of the vials has been reconstituted in this manner, the total dose may be administered to the person from the common reservoir or syringe. Reconstituting lyophilized drug from two or more vials in this manner is, however, relatively time consuming. Furthermore, there is a risk of contamination of the drug due to the number of times a free opening will be exposed to free air or dirt.

It is therefore desirable to provide a drug mixing device which facilitates mixing a dose using lyophilized drug from two or more vials, and which reduces the risk of contamination of the resulting drug.

DISCLOSURE OF THE INVENTION

Having regard to the above-identified problems and deficiencies, it is an object of the present invention to provide a simple but efficient mixing device for mixing the contents of two containers and for transferring the mixed solution to a standard syringe.

In a first aspect, the invention is provided by a transfer system comprising:
  a housing;
  a first port in said housing adapted to receive a first container having first contents therein;
  a second port in said housing adapted to receive a second container that contains second contents to be mixed with the first contents to form a material;
  a third port for coupling to a syringe, the third port being in fluid communication with the second port;
  a first channel that enables the second contents from the second container to move to the first container;
characterized in that the transfer system further comprises:
  a second channel that enables the contents of the first container to move to the third port;
  a first flow control member disposed between the third port and the second port, enabling one-way fluid flow between a syringe and the second port when said syringe is coupled to the third port; and
  a second flow control member, enabling selective fluid flow from the first port to a syringe coupled to the third port, via said second channel, thereby allowing a material formed by mixing the first contents of the first container and the second contents of the second container to flow into the syringe.

In the present context the term 'housing' should be interpreted to mean a part of the system which is adapted to hold at least the first port, the second port and the third port, the mutual spatial position of these ports thereby being substantially fixed. Furthermore, the housing is preferably adapted to accommodate the channels, in which case appropriate fluid connections between containers and syringe are established when suitable containers and syringe are positioned at the respective ports.

Preferably, the first contents is a dry material, such as a powdered or lyophilized drug, and the second contents is a liquid material, such as a diluent which is suitable as a solvent for the first contents. In this case the material formed when the first contents and the second contents are mixed is a reconstituted drug being ready for delivery to a user, e.g. by means of infusion or injection. Alternatively, the first contents as well as the second contents may be liquid materials.

The first container may be any suitable kind of container, such as a vial, a flexible container, such as a bag, etc. Similarly, the second container may be any suitable kind of container as defined above.

The third port is in fluid communication with the second port. Accordingly, it is possible to move fluid between a syringe coupled to the third port and a container coupled to the second port. Depending on the specific configuration of the transfer system it may be possible to move fluid in either direction between the third port and the second port. It may even be possible to selectively move fluid in both directions, e.g. at different times during an operation procedure of the system.

The first channel enables the second contents from the second container to move to the first container. Accordingly, the first channel establishes a direct fluid connection between the first container and the second container, and when the second contents is moved from the second container to the first container via the first channel, the first contents and the second contents mix, and thereby the material is formed.

The second channel enables the contents of the first container to move to the third port. Thus, the second channel establishes a fluid connection between the first port and the third port. When the first contents and the second contents have been mixed, the resulting material may thereby be transferred from the first container to a syringe coupled to the third port. Accordingly, the material may subsequently be delivered using the syringe. Furthermore, the second channel may be used for moving air from the first container to the syringe in order to reduce the pressure in the first container. Such a reduced pressure may help in moving second contents from the second container to the first container via the first channel.

It should be noted that the second channel may also allow for a fluid flow in an opposite direction, i.e. from the third port towards the first port. Thereby it may be possible to transfer fluid from a syringe to a container coupled to the first port.

The first flow control member enables one-way fluid flow between a syringe, coupled to the third port, and the second port. Thus, the first flow control member may either enable fluid flow in a direction from the syringe towards the second port, or in a direction from the second port towards the syringe. In the case that the first flow control member enables a fluid flow in a direction from the syringe towards the second port, this may advantageously be used for transferring a fluid, e.g. air, from the syringe to the second container, thereby increasing the pressure in the second container. Such an increased pressure may cause the second contents to move from the second container to the first container via the first channel. In the case that the first flow control member enables a fluid flow in a direction from the second port towards the syringe, this may, e.g., be used for transferring the second contents from the second container to the syringe. The second contents may then be transferred from the syringe to the first container. It should be noted that the first flow control member may be adapted to enable one-way fluid flow in both directions, e.g. at different times during operation of the transfer system.

The second flow control member enables selective fluid flow from the first port to a syringe coupled to the third port, via the second flow channel. Thereby, material formed by mixing the first contents and the second contents is allowed to flow into the syringe. This is an advantage because the mixed material may then be delivered by means of the syringe. Furthermore, the second flow control member ensures that transfer of the mixed material takes place at a desired time, e.g. not before it has been ensured that the first contents and the second contents have been properly mixed.

The second flow control member may comprise a gate valve.

According to one embodiment, selective fluid flow through the second flow control member may be enabled when the fluid pressure in the third port exceeds a predefined negative pressure. According to this embodiment, the mixed material may advantageously be moved from the first container to the syringe due to a decrease in pressure at the third port. Such a decrease in pressure may be obtained by pulling back a piston of the syringe. The second flow control member may, in this case, advantageously be a check valve, e.g. of a kind which is spring biased. When the pressure difference between a pressure level at the first port and a pressure level at the third port becomes sufficiently large to overcome the spring force, the valve will open, thereby allowing the mixed material to move from the first container to the syringe.

The first flow control member may provide selective fluid flow through the first flow control member. In this case the selective fluid flow through the first flow control member may be enabled when the fluid pressure in the third port exceeds a predefined fluid pressure. This is similar to the situation described above. Alternatively, fluid flow through the first flow control member may be disabled when fluid flow through the second flow control member is enabled. In this case, when the fluid flow is enabled through the second flow control member and the mixed material is thereby allowed to flow from the first container to the syringe, a fluid flow through the first flow control member is automatically disabled. Thereby it can be ensured that no fluid can flow between the syringe and the second container during transfer of the mixed material from the first container to the syringe.

The first port and/or the second port may be adapted to releasably couple to vial(s) having a piercable septum, thereby allowing fluid flow to and from the vials when the vials are coupled to the first and/or second port. According to this embodiment, it is possible to replace vials coupled to the ports, and pooling of vials is therefore very easy.

The first flow control member may enable fluid flow from a syringe to the second container, a fluid flow enabled by the first flow control member thereby causing an increase in pressure in the second container. Such an increase in pressure will normally help in forcing the second contents of the second container towards the first container, i.e. the second contents will in this case be moved due to a difference in pressure levels between the first container and the second container.

Alternatively, the first flow control member may enable fluid flow from the second container to a syringe, a fluid flow enabled by the first flow control member thereby causing the second contents to move from the second container to the syringe. According to this embodiment, the second contents are sucked into the syringe via the first flow control member. Subsequently, the second contents may be transferred from the syringe to the first container in order to cause the first contents and the second contents to mix.

Thus, the second contents may be enabled to move from the second container to the first container via the first channel due to a difference in pressure between a pressure in the first container and a pressure in the second container. The pressure difference may be at least partly provided by increasing the pressure in the second container and/or the pressure difference may be at least partly provided by decreasing the pressure in the first container. Alternatively or additionally, the pressure difference may be at least partly provided by using a first container which is delivered with a low pressure, i.e. which has initially been positioned under vacuum.

The transfer system may further comprise a first filter arranged in a flow path between the third port and an inlet of the housing. This is particularly advantageous if the transfer system functions in such a manner that air is forced into the second container by means of the syringe in order to increase the pressure in the second container. Such air must initially be sucked into the syringe, and since ambient air may be contaminated and/or contain undesired impurities it is an advantage that it is sucked into the syringe via a filter. Thereby the risk of contamination of the drug is minimised.

Alternatively or additionally, the transfer system may further comprise a second filter arranged in the second channel. Such a filter can advantageously be used for preventing impurities from being transferred from the first container to the syringe when the mixed material is transferred to the syringe. Such impurities could, e.g., be rubber particles originating from a stopper of a vial and being created during penetration of the stopper, and/or dry contents which have not been properly solved. It is undesirable that an injectable drug contains such impurities, and it is therefore an advantage to remove them by means of a filter.

According to a second aspect of the invention there is provided a method for forming a drug, the method comprising:
  providing a transfer system;
  providing a first container having a first contents therein and a second container having a second contents therein;
  inserting the first container into a first port of the transfer system, and the second container into a second port of the transfer system;
  providing a difference in pressure between a pressure of the first container and a pressure of the second container, said difference in pressure enabling at least a fraction of the second contents to move from the second container to the first container, via a first channel, to form a solution in the first container; and
  activating a second flow control member, thereby moving the formed solution from the first container to a syringe coupled to a third port of the transfer system.

The transfer system may advantageously be a transfer system according to the first aspect of the invention. However, one or more of the features described in combination with the first aspect of the invention may be omitted in the transfer system provided according to the second aspect of the invention.

The step of providing a difference in pressure may comprise:
  metering a predefined amount of air in the syringe and coupling the syringe to the third port; and
  expelling at least a fraction of the air contained in the syringe thereby moving the expelled air to be received in the second container and thereby increasing the pressure in the second container.

According to this embodiment, the difference in pressure is at least partly provided by increasing the pressure in the second container, and the increase in pressure is obtained by forcing air into the second container by means of the syringe.

Alternatively or additionally, the step of providing a difference in pressure may comprise decreasing the pressure in the first container. This may, e.g., be obtained by sucking air out of the first container, e.g. using the syringe.

The method may further comprise the steps of:
  deactivating the second flow control member, thereby disabling fluid flow through the second flow control member;
  removing the first container from the first port and removing the second container from the second port;
  providing a new first container having a first contents therein, and a new second container having a second contents therein;
  inserting the new first container into the first port and the new second container into the second port;
  providing a difference in pressure between a pressure of the first container and a pressure of the second container, said difference in pressure enabling at least a fraction of the second contents to move from the second container to the first container, via a first channel, to form a solution in the first container; and
  activating the second flow control member, thereby moving the formed solution from the first container to the syringe.

According to this embodiment two or more sets of containers are sequentially coupled to the first and second ports, their contents are mixed to form a material, and the material is transferred to the syringe. Accordingly, the resulting amount of mixed material in the syringe when the procedure is finished corresponds to the contents of two or more sets of containers.

Thus, according to this embodiment, a dose of drug which is larger than what corresponds to the contents of a single set of containers can be mixed and collected in the syringe, i.e. pooling of the contents of several containers is possible. Furthermore, the method steps may be performed as many times as necessary in order to mix a dose of a desired amount of drug.

The method may further comprise the steps of:
  decoupling the syringe from the third port;
  providing a new transfer system;
  providing a first container having a first contents therein, a second container having a second contents therein and a syringe;
  inserting the first container into a first port of the transfer system, and the second container into a second port of the transfer system;
  coupling the syringe to a third port of the transfer system;
  providing a difference in pressure between a pressure of the first container and a pressure of the second container, said difference in pressure enabling at least a fraction of the second contents to move from the second container to the first container, via a first channel, to form a solution in the first container; and
  activating a second flow control member, thereby moving the formed solution from the first container to the syringe.

This embodiment also enables pooling of the contents of two or more container sets. However, in this case the transfer system is not reused.

The method may further comprise the step of decoupling the syringe from the third port. Thereby it is possible to subsequently deliver the mixed material using the syringe. This may, e.g., be done by:

providing an infusion set; and coupling the infusion set to the syringe thereby forming a fluid delivery device.

According to a third aspect of the invention there is provided a drug mixing kit comprising:

a container unit comprising a first container, said first container containing first contents, and a second container, said second container containing second contents to be mixed with the first contents to form a material, and a transfer unit comprising first and second ports adapted to receive first and second containers of a container unit, and a third port for coupling to a syringe, the transfer unit further comprising a number of flow channels, at least some of the flow channels pair-wise interconnecting two of the first port, the second port and the third port, wherein the container unit and the transfer unit are adapted to be coupled together to form a drug mixing kit.

It should be noted that a skilled person would readily recognise that any feature described in combination with the first aspect of the invention could also be combined with the second or third aspects of the invention, any feature described in combination with the second aspect of the invention could also be combined with the first and the third aspects of the invention, and any feature described in combination with the third aspect of the invention could also be combined with the first and second aspects of the invention.

The container unit holds the first and second containers. The containers are positioned in the container unit by the manufacturer, and it can thereby be ensured that the first contents and the second contents match, e.g. in terms of amount and kind. Accordingly, when the first contents and the second contents are mixed, the risk of errors occurring during mixing of the contents is thereby minimised.

The transfer unit may be or comprise a transfer system according to the first aspect of the invention. However, it may also be envisaged that other kinds of transfer units could be used. For instance, the flow channels may interconnect the ports in a different manner than the one described with reference to the first aspect of the invention.

The container unit and the transfer unit are adapted to be coupled together to form a drug mixing kit. The units may advantageously be delivered together in one package. In order to mix the first contents and the second contents, the user must couple the units together, and possibly operate one or more features of the transfer unit, e.g. one or more flow control members and/or a piston of a syringe, in order to cause the first contents to move to the second container or the second contents to move to the first container. Thereby the container unit may be maintained under sealed conditions during storage. This increases the expected lifetime for the contents of the containers, and counteracts contamination of the contents.

Furthermore, by providing the container unit and the transfer unit as a kit it can be ensured that the transfer unit is actually suitable for mixing the contents of the first and second containers.

The container unit and the transfer unit may be shaped in such a manner that they can only be coupled together when being positioned at a predetermined mutual orientation. According to this embodiment, it can be ensured that the first container is coupled to the first port and the second container is coupled to the second port when the container unit and the transfer unit are coupled together. Thereby it is also ensured that the first container, the second container and the syringe are interconnected in a correct manner by the flow channels, and that the fluid flows in the transfer unit during mixing of the first and second contents are as expected. Accordingly, a correct mixing of the first contents and the second contents can be ensured.

The feature described above may, e.g., be provided by shaping the container unit and the transfer unit in an asymmetric manner, e.g. having a straight edge and a curved edge opposing the straight edge.

The transfer unit may comprise a first channel fluidly connecting the first port and the second port, thereby enabling the second contents of a second container received in the second port to move to a first container received in the first port. This has already been described above with reference to the first aspect of the invention.

Alternatively or additionally, the transfer unit may comprise a second channel fluidly connecting the first port and the third port, thereby enabling fluid flow between the first port and the third port. According to this embodiment, a mixed material formed in a first container coupled to the first port can be transferred to a syringe coupled to the third port. This has already been described above with reference to the first aspect of the invention. The transfer unit may comprise a second flow control member arranged in the second channel, said second flow control member enabling selective fluid flow between the first port and the third port.

Alternatively or additionally, the transfer unit may comprise a third channel fluidly connecting the second port and the third port, thereby enabling fluid flow between the second port and the third port. The transfer unit may, in this case, comprise a first flow control member arranged in the third channel, said first flow control member enabling selective fluid flow between the second port and the third port. This has also been described above with reference to the first aspect of the invention.

Also, in further aspects of the invention the transfer system includes preassembled transfer systems each of which comprises a transfer device according to any of the embodiments disclosed herein, a diluent container and a drug container accommodating a lyophilized drug, where the two containers are inserted into the housing of the transfer thereby forming a preassembled unit but where the fluid communication to and from the vials have not yet been established. In use, a syringe, preferably containing an amount of air, is coupled to the transfer device whereafter fluid communication to and from the vials of the particular preassembled transfer system can be established and the reconstitution forming sequence can take place.

If a dose is required which can not be accomplished with a single preassembled transfer system, one or more additional preassembled transfer systems can be sequentially used with the same syringe, provided that the syringe has a volume for accommodating the total appropriate amount of the drug solution. Preferably for such systems, different sets of preassembled transfer system sets can be supplied to the user, wherein the different sets contain a dose corresponding to a number of preselected dose amounts.

BRIEF DESCRIPTION OF THE DRAWINGS

In the following the invention will be further described with references to the drawings, wherein.

DESCRIPTION OF EXEMPLARY EMBODIMENTS

The present invention is directed to drug delivery systems and methods. The drug delivery system provides generally for the delivery of a drug in solution under pressure, and more particularly to the injection of powdered or lyophilized drugs that require reconstitution. The drug delivery system includes a reconstitution system, a pressurization system to facilitate drug delivery, a transfer system and an injector system. Different embodiments of the present invention may use only one of the systems described and other embodiments can employ combination of these systems, depending on the requirements of different applications. For example, a preferred embodiment can deliver a liquid drug and not require reconstitution. Therefore the drug delivery systems and methods are a combination of some or all of the systems or processes described below.

Firstly, with reference to FIGS. 1, 10 and 11 an embodiment of a transfer system for forming a drug solution will be described focusing primarily on the directly user-oriented features.

Figure 1:
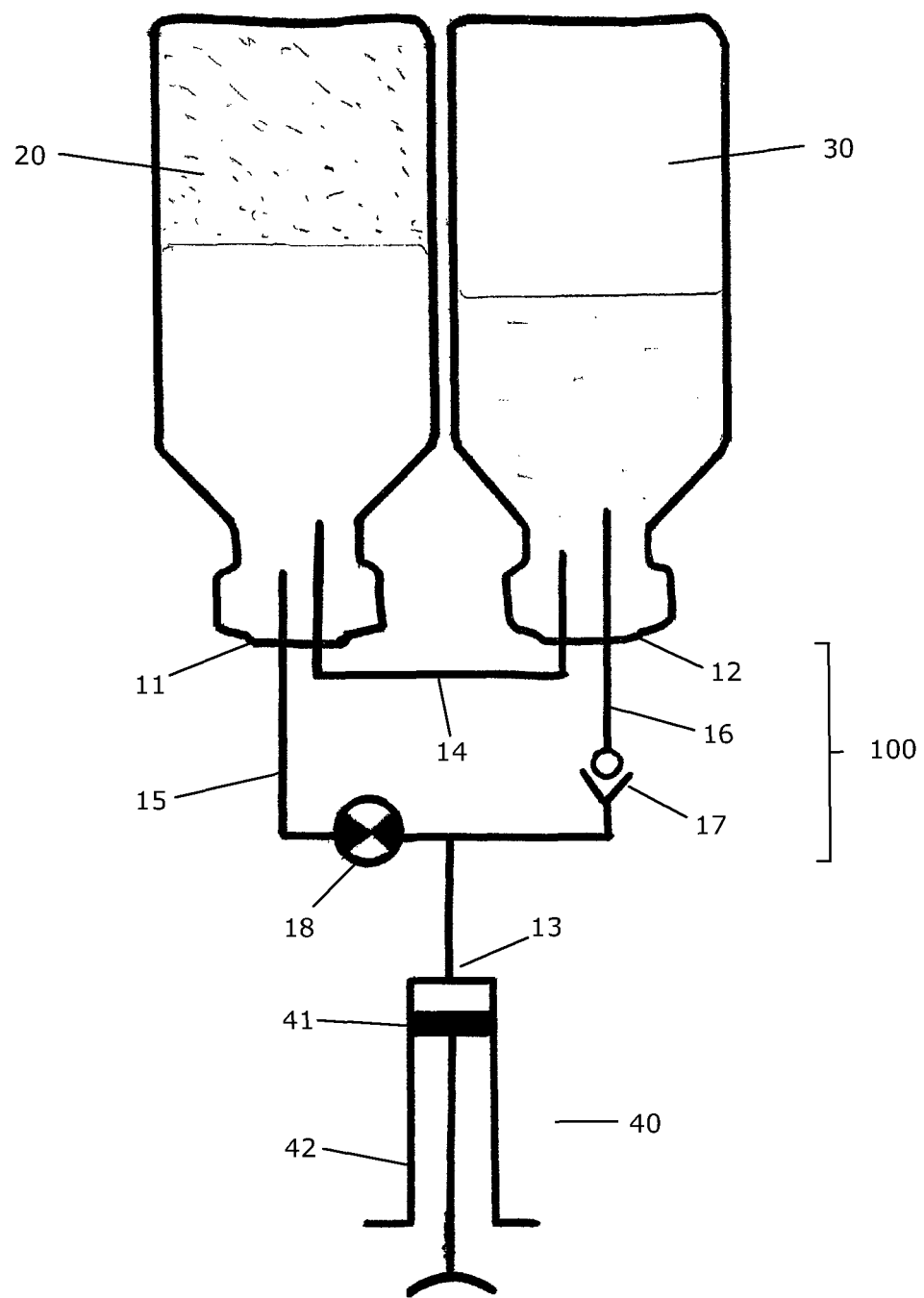
FIGS. 1-9 are schematic views of transfer systems according to various embodiments according to the invention.

FIG. 1 is a schematic representation of a transfer system 100 connected to a first container 20 containing a predetermined amount of a lyophilized drug or powder, a second container 30 containing a predetermined amount of a diluent. Also shown in FIG. 1 is a syringe 40 connected to transfer system 100.

In the depicted embodiment, the two containers 20 and 30 are formed as standard vials each having a piercable septum closing the vial and having a retaining cap for fixedly retaining the septum.

Transfer device 100 contains a housing 10 (see FIG. 10) which houses both the necessary fluid lines, control members and the containers 20 and 30. The housing 10 may be designed to receive the two containers 20 and 30, so that they are partly or fully accommodated inside the housing 10. Alternatively, the housing 10 may be designed to only encircle cap part of the vials.

Transfer device 100 is provided with a first port 11 for coupling to container 20 and a second port 12 adapted to couple to container 30. The coupling of the ports 11 and 12 may be adapted to receive each of the two containers in a first condition and a second condition. In the first condition, the two containers are only retained in the housing and no fluid communication to the interior of the two containers is established. In this first condition, the transfer system, including the two containers, can be long term stored. In the second condition fluid communication is established between the fluid lines of transfer device 100 and containers 20 and 30.

The coupling ports 11 and 12 may contain any means of providing fluid communication with the inside of the containers 20 and 30, such as hollow needles, hollow spikes etc. Preferably, if needles or spikes penetrating the septum are used, the needles or spikes are so formed that substantially no residual liquid can be trapped inside the containers 20 and 30.

Housing 10 further comprises coupling means in the form of a third port 13 for releasably coupling a syringe 40 having a sealing plunger 41 slideable mounted inside barrel 42. Preferably, the open (distal) end of syringe 40 comprises means for releasably attaching a conduit by a releasable connector, such as a luer connector of an infusion set. Accordingly, housing 10 comprises corresponding connection means for releasably connecting the syringe 40 to the third port 13.

FIG. 1 further shows a first channel 14 that enables fluid communication between first container 20 and second container 30. Further, first port 11 and third port 13 are in fluid communication via a second channel 15. Also, second port 12 and third port 13 are in fluid communication via a third channel 16.

At one point along third channel 16, a first flow control member 17, preferably in the form of a check valve or non-return valve, is provided resulting in a one-way flow from port 13 to port 12.

At one point along second channel 15, a second flow control member 18, preferably in the form of a check-valve, is provided. In its closed position, fluid communication is disabled while in its open position fluid flow from port 11 to port 13 can be obtained.

The remaining parts of transfer device and of the containers are not shown or described here, but are considered the object of a normal design procedure performed by the skilled person along the lines set out in the present specification.

Figure 10:
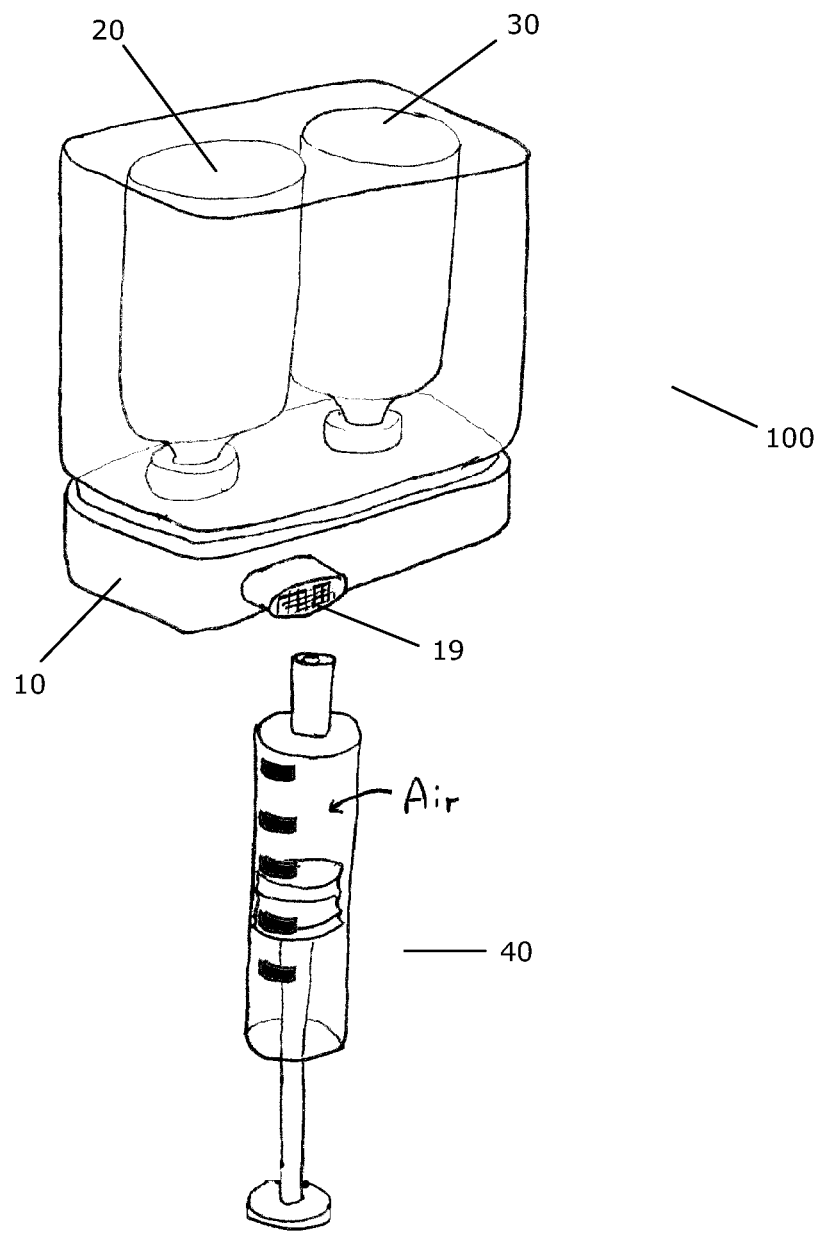
FIG. 10 shows a perspective view of the embodiment shown in FIG. 1.

FIG. 10 shows a perspective, partly transparent view of transfer system 100 where containers 20 and 30 are received in the housing 10.

In operation, prior to connecting syringe 40, the user pulls back the piston 41 so as to meter a prescribed amount of air into syringe 40. The amount of air may correspond to at least the volume of diluent in container 30.

Thereafter, syringe 40 is connected to the transfer system 100 by coupling the distal end of the syringe 40 to the third port 13. Also, containers 20 and 30 are brought into a state providing fluid communication to ports 11 and 12. The state of second flow control member 18 is set to its closed position. By expelling air from syringe 40, air is moved via check-valve 17 via channel 16 to the second container 30. As pressure increases in container 30, diluent is transported via first channel 14 into container 20 comprising the lyophilized drug. Depending on the amount of air that is pushed into transfer system 100, a fraction of the diluent is forced into the first container 20. If an amount of air is expelled which generally corresponds to the volume of diluent in container 30, around half of the diluent will be forced into first container 20. Once reconstituted, the solution can be moved from first container 20 into syringe 40 by appropriately changing the state of the second flow control member 18 into its open condition by manipulating a button or knob 19 controlling second flow control member 18. The increased pressure provided in the system will automatically force the solution through the third port 13 and into the syringe 40, thereby also forcing the piston 41 towards the proximal end. However, also manually pulling the piston 41 towards the proximal end of syringe 40 may facilitate fluid transport of any remaining fluids in the transfer system.

As the formed reconstituted solution is transported from the first container 20 into the syringe 40, remaining diluent in second container 30 is transported to the first container 20. The continuous dilution of the solution will ensure a flushing effect on any residual solution adhering to the internal walls of container 20 and internal walls of the flow elements situated between first port 11 and third port 13.

The fluid channel leading from third port 13 to second port 12 may be provided with a gate valve thereby avoiding any of the solution to move through check valve 17. This gate valve (not shown) may be operated manually by an operable control button or the like. Preferably, this gate valve is controlled simultaneously when the second flow control member 18 is operated. The operation of the two gate valves may be obtained by any appropriate mechanical connection.

In a further variant, the channel leading from third port 13 to second port 12 is provided with a flow control valve being controlled by the fluid pressure in the channel 16. The flow control valve can be designed to remain closed when fluid pressure is below a certain limit and to enable fluid communication when exceeding this limit.

Also, the second flow control member 18 may be adapted to only enable fluid communication when fluid pressure in third port 13 is exceeding a certain negative fluid pressure limit.

If the amount of the above described reconstituted solution is not sufficient for one administration, the contents of the reconstituted solution inside syringe 40 may be accumulated by a subsequent mixing. This may be obtained by several schemes using the same transfer system 100 or using one or more similar transfer systems 100' and 100".

If the same transfer system 100 is used as already used for the initial mixing procedure as described above, the syringe 40 may initially be adjusted to accommodate enough air for all subsequent mixing procedures. Then, the containers 20 and 30 may be interchanged by removing the empty containers 20 and 30 and inserting new containers 20 and 30, and the mixing procedure may be repeated in the same way as described above.

Figure 11:
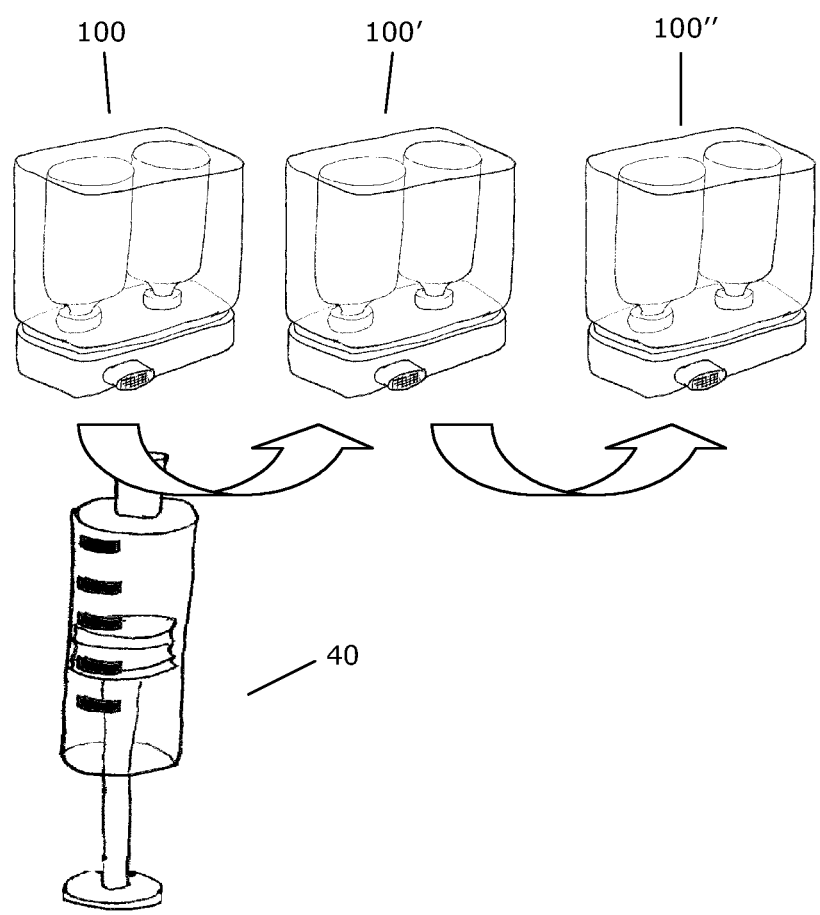
FIG. 11 shows a perspective view of an additional embodiment of the invention.

An alternative embodiment is depicted in FIG. 11 which shows one syringe 40 sized to accommodate the contents of three vial sets from three transfer systems. Preferably, in this embodiment, each transfer system is supplied to the user as a preassembled transfer system including vial set 20 and 30, wherein the particular vial set corresponds to a dose amount selected from a number of available dose amounts. As indicated in FIG. 11, syringe 40 initially is connected to transfer system 100 for transferring the reconstituted solution of the included vials 20 and 30 into syringe 40. Next, the syringe is connected to a new transfer system 100' accumulating the reconstituted solution of vials 20 and 30 of transfer system 100' into syringe 40, and finally the syringe 40 is connected to transfer system 100" for accumulating the contents of this preassembled transfer set.

Prior to the reconstitution scheme just described, the syringe 40 may be filled with air corresponding to the volume necessary for forcing all the contents of transfer systems 100, 100' and 100". Alternatively, prior to connecting the syringe 40 to a new transfer system, the syringe 40 may be filled with an amount of air just necessary for forcing the contents of the consecutive transfer system into the syringe 40.

After the necessary dose amount has been accumulated, the syringe 40 is detached from the particular transfer system, whereafter administration of the medicament contained in syringe 40 can take place.

The transfer system as described above may be packed as a kit containing containers 20 and 30 seated in the housing 10 of transfer system 100 ready for fluid coupling to the ports 11 and 12. Also, the kit may comprise a syringe of a given size, an infusion set comprising a butterfly needle, a port, a cath set, or alternatively, a needle for connecting with the syringe 40.

As a further alternative, the transfer system 100 of the invention may be provided with coupling means for coupling an infusion set directly to the transfer system 100. In such a system the port 13 may be provided with valve means directing the expelled reconstituted solution from syringe 40 when still connected to the transfer system 100 towards the infusion set.

Figure 2:
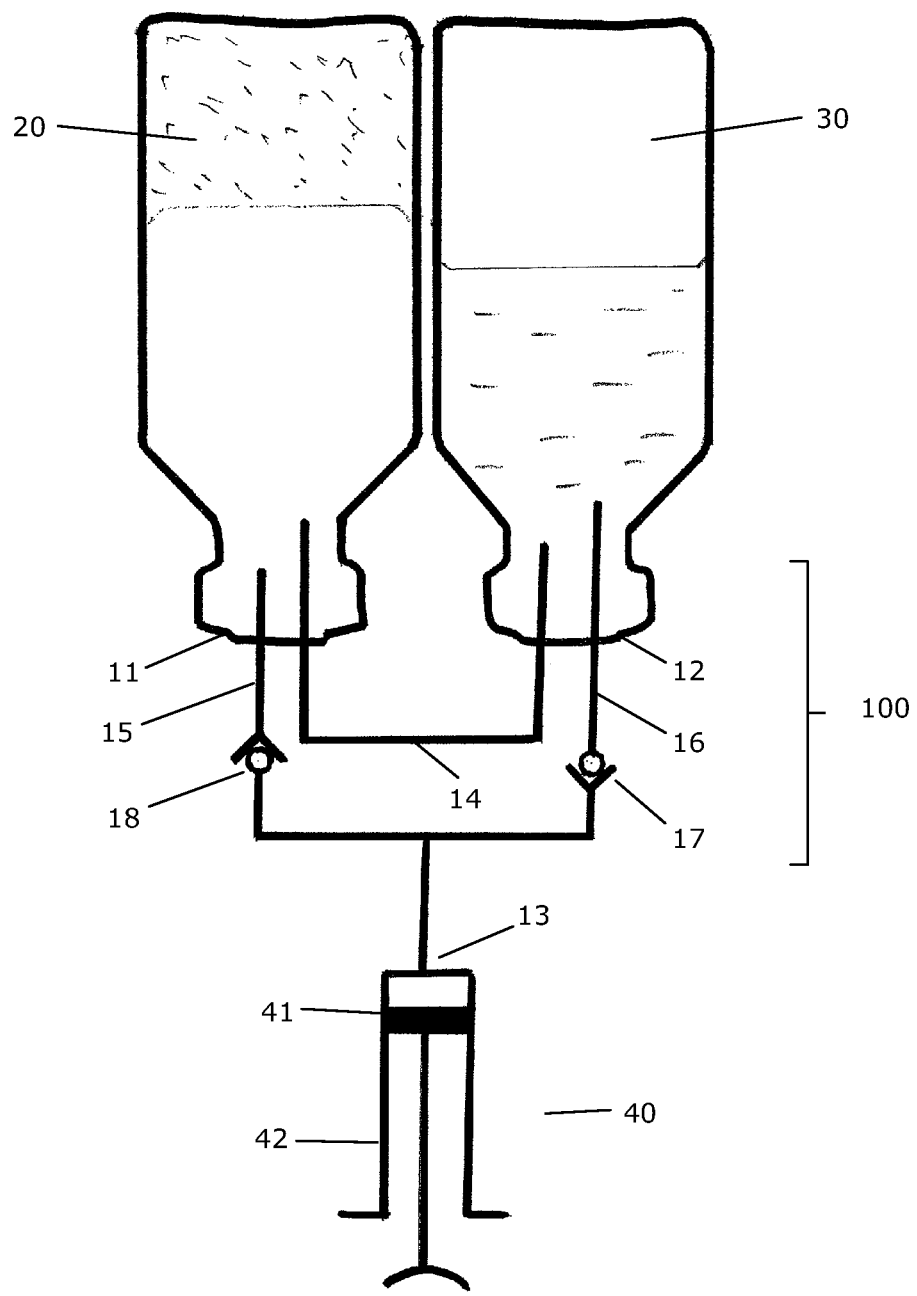

FIG. 2 is a schematic view of a second embodiment of a transfer system 100 according to the invention. The embodiment of FIG. 2 is very similar to the embodiment of FIG. 1, and the fundamental operation of the transfer system 100 will therefore not be described in further detail here.

In FIG. 2 the second flow control member 18 is an ordinary check valve which is operated by a difference in pressure at the first port 11 and at the third port 13. Accordingly, when the piston 41 of the syringe 40 is pulled back, the second control member 18 will open, and reconstituted drug is transferred from the first container 20 to the syringe 40.

Figure 3:
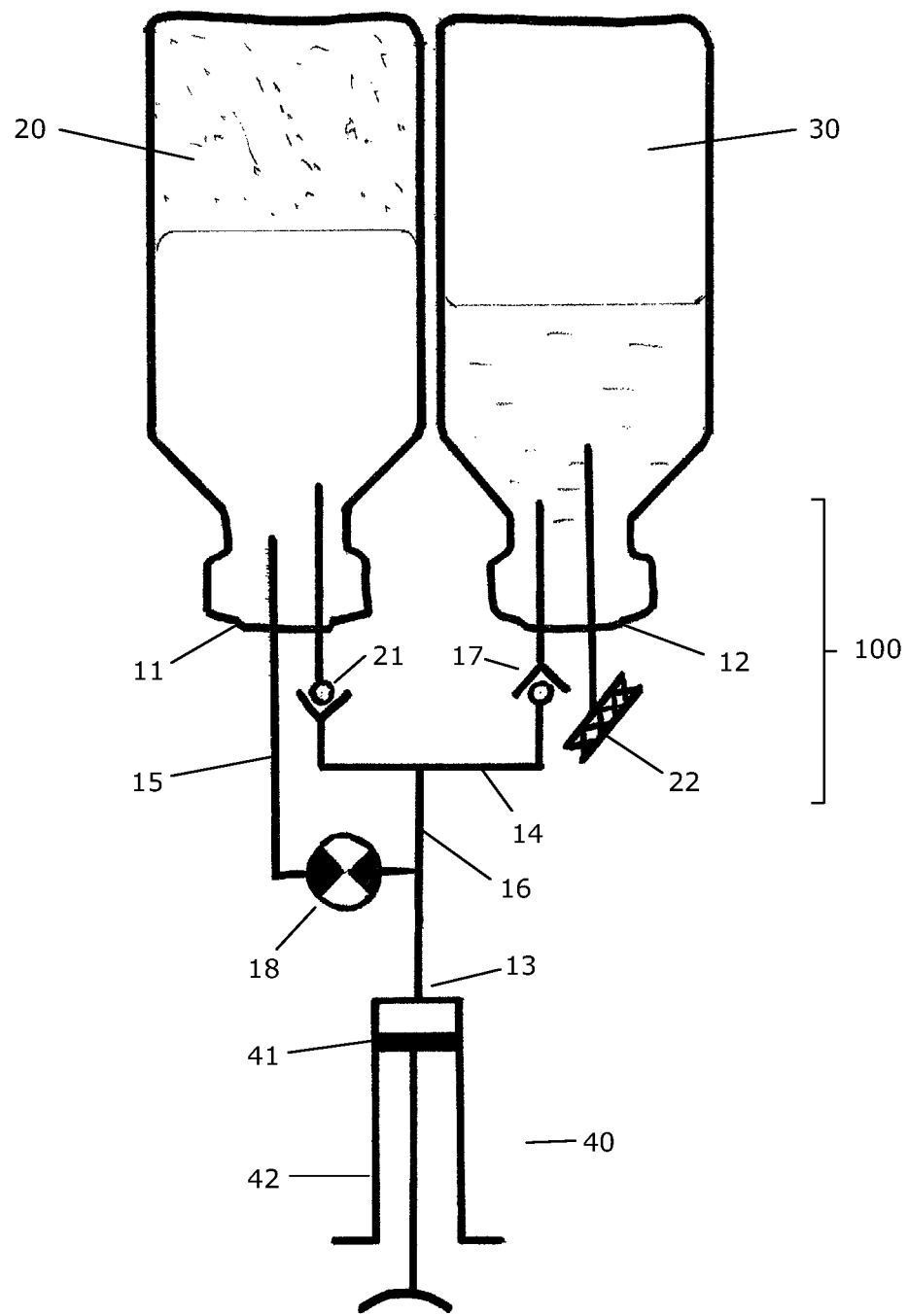

FIG. 3 is a schematic view of a third embodiment of a transfer system 100 according to the invention. The parts of the transfer system 100 of FIG. 3 which are identical to parts which have previously been described with reference to the preceding Figures will not be described in further detail here.

The transfer system 100 of FIG. 3 may be operated in the following manner. When it is desired to mix the contents of the first container 20 and the contents of the second container 30, it is first ensured that the second flow control member 18 is closed. Then the piston 41 of the syringe 40 is pulled back. This will cause check valve 17 to open while check valve 21 remains closed. Accordingly, liquid is sucked out of the second container 30 and into the syringe 40 via the third channel 16. Furthermore, ambient air is sucked into the second container 30 via filter 22. The check valve 21 ensures that air or material is not sucked from the first container 20 into the syringe 40 during this operation. The fact that the inlet connected to the filter 22 is arranged above the outlet connected to the third channel 16 ensures that no air bubbles are transferred along with the liquid from the second container 30 to the syringe 40.

When a sufficient amount of liquid has been transferred to the syringe 40, the piston 41 is pushed forward. This will close check valve 17 while check valve 21 opens. Accordingly, liquid is transferred from the syringe 40 to the first container 20, and the first contents and the second contents are thereby allowed to mix. The transfer of liquid into the first container 20 causes an increase in pressure in the first container 20. Check valve 21 and the closed second flow control member 18 prevents the liquid from leaving the first container 20.

When it has been established that the first contents and the second contents have mixed properly, the second flow control member 18 is opened, and the increased pressure in the first container 20 forces the mixed material out of the first container 20 and into the syringe 40 via the second channel 15.

Figure 4:
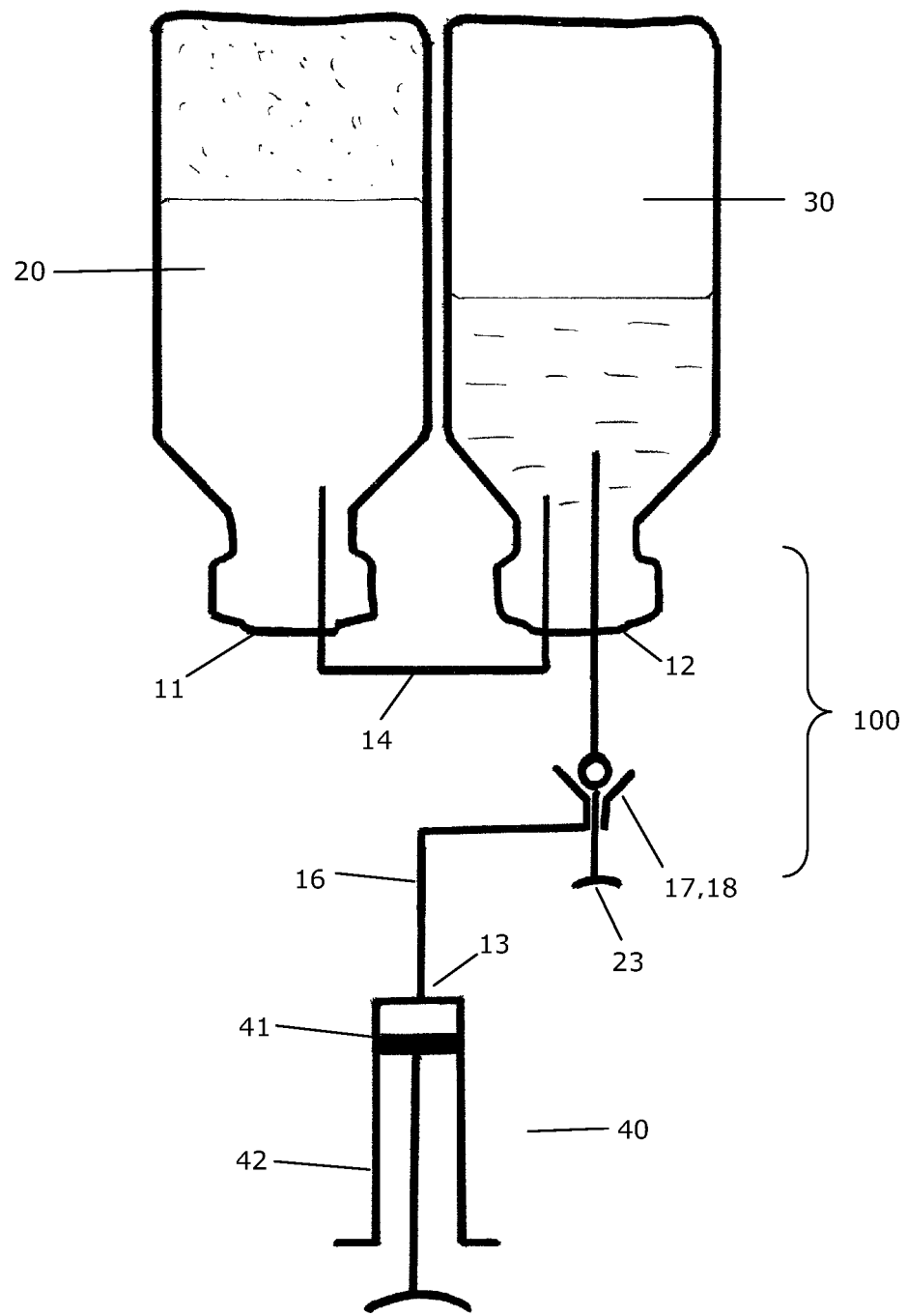

FIG. 4 is a schematic view of a fourth embodiment of a transfer system 100 according to the invention. The parts of the transfer system 100 of FIG. 4 which are identical to parts which have previously been described with reference to the preceding Figures will not be described in further detail here.

The transfer system 100 of FIG. 4 may be operated in the following manner. When it is desired to mix the contents of the first container 20 and the contents of the second container 30, air is initially sucked into the syringe 40 by pulling the piston 41 back, and the syringe 40 is then coupled to the third port 13. Then the piston 41 is pushed forward. This causes check valve 17, 18 to open, and air is transferred from the syringe 40 into the second container 30 via channel 16, thereby increasing the pressure in the second container 30. The increased pressure in the second container 30 causes the second contents to be transferred from the second container 30 to the first container 20, via the first channel 14, thereby allowing the first contents and the second contents to mix. The pressure in the first container 20 increases during this operation.

When it has been established that the first contents and the second contents have mixed properly, the flow control member 17, 18 is manually opened by pushing button 23. The increased pressure in the containers 20, 30 then causes the mixed material to be transferred to the syringe 40 via channels 14, 16. The pressure difference between the containers 20, 30 and the syringe 40 may be further increased by pulling the piston 41 slightly backwards.

Figure 5:
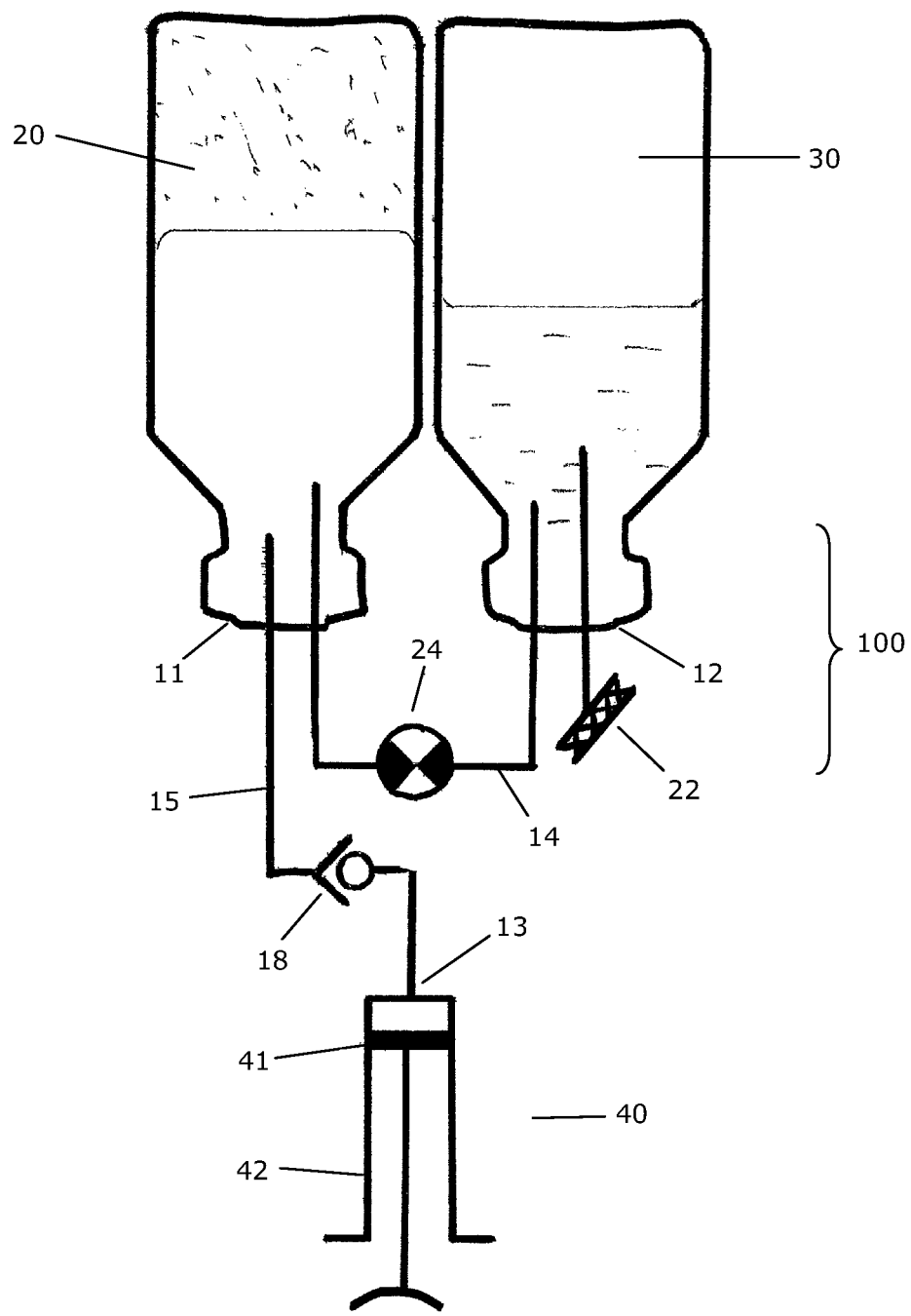

FIG. 5 is a schematic view of a fifth embodiment of a transfer system 100 according to the invention. The parts of the transfer system 100 of FIG. 5 which are identical to parts which have previously been described with reference to the preceding Figures will not be described in further detail here.

The transfer system 100 of FIG. 5 may be operated in the following manner. When it is desired to mix the contents of the first container 20 and the contents of the second container 30, it is first ensured that valve 24 is closed, and then the piston 41 of the syringe 40 is pulled back. This causes check valve 18 to open, and air is sucked from the first container 20 into the syringe 40 via channel 15, thereby decreasing the pressure in the first container 20. Then the valve 24 is opened, and the difference in pressure between the first container 20 and the second container 30 causes liquid to be transferred from the second container 30 to the first container 20, via channel 14. During this, ambient air is sucked into the second container via filter 22.

When it has been established that the first contents and the second contents have mixed properly, the piston 41 is pulled back, thereby causing the mixed material to be transferred from the first container 20 to the syringe 40 via channel 15.

Figure 6:
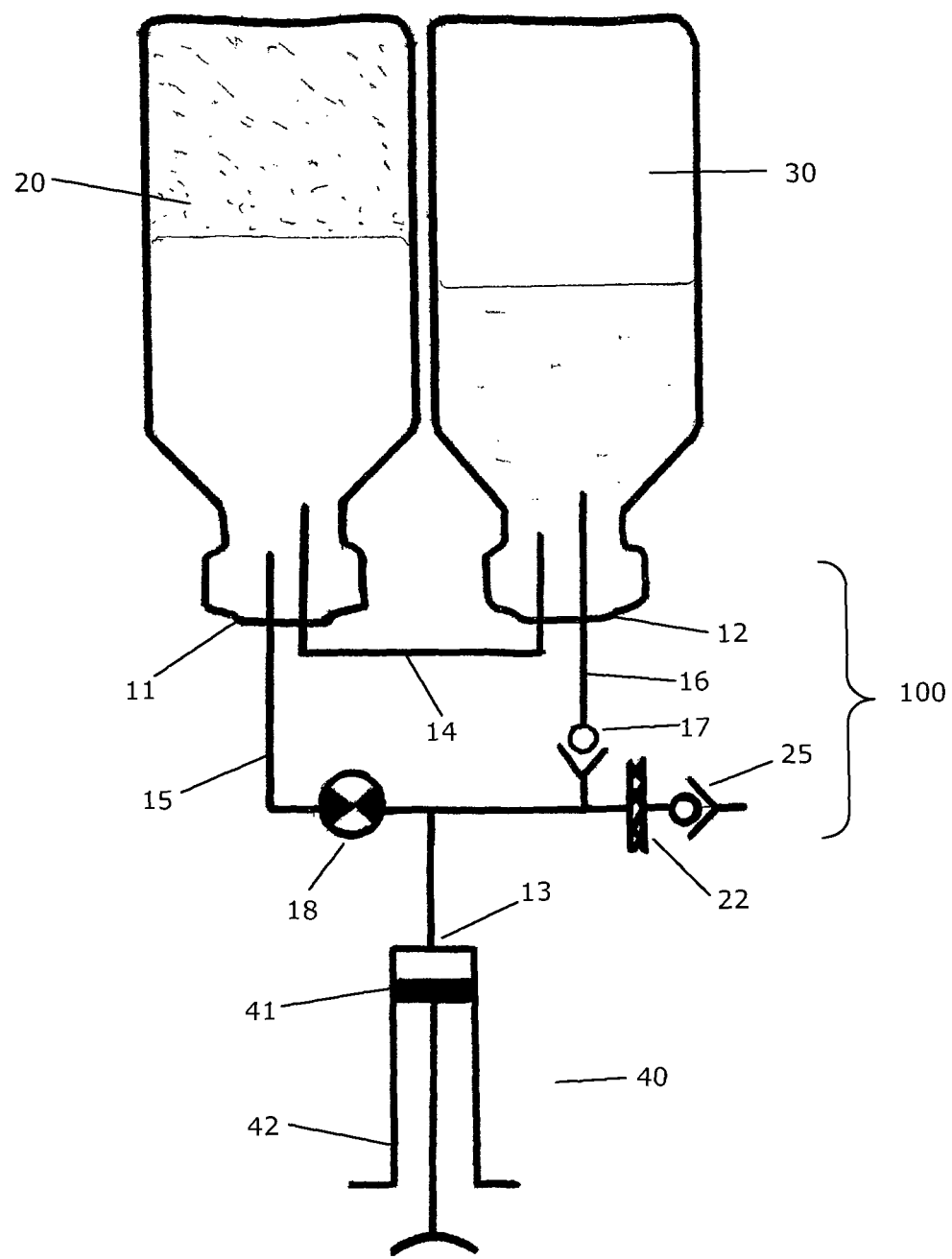

FIG. 6 is a schematic view of a sixth embodiment of a transfer system 100 according to the invention. The parts of the transfer system 100 of FIG. 6 which are identical to parts which have previously been described with reference to the preceding Figures will not be described in further detail here.

The transfer system 100 of FIG. 6 is very similar to the transfer system 100 of FIG. 1, and it is operated in substantially the same manner. However, in the transfer system 100 of FIG. 6, ambient air is initially sucked into the syringe 40 via filter 22 by pulling the piston 41 back. Thereby it is ensured that the air entering the syringe 40, and thereby the transfer system 100, is not contaminated. When the air is subsequently forced into the second container 30 as described above, check valve 25 ensures that the air does not leave the transfer system 100 via the filter 22.

Figure 7:
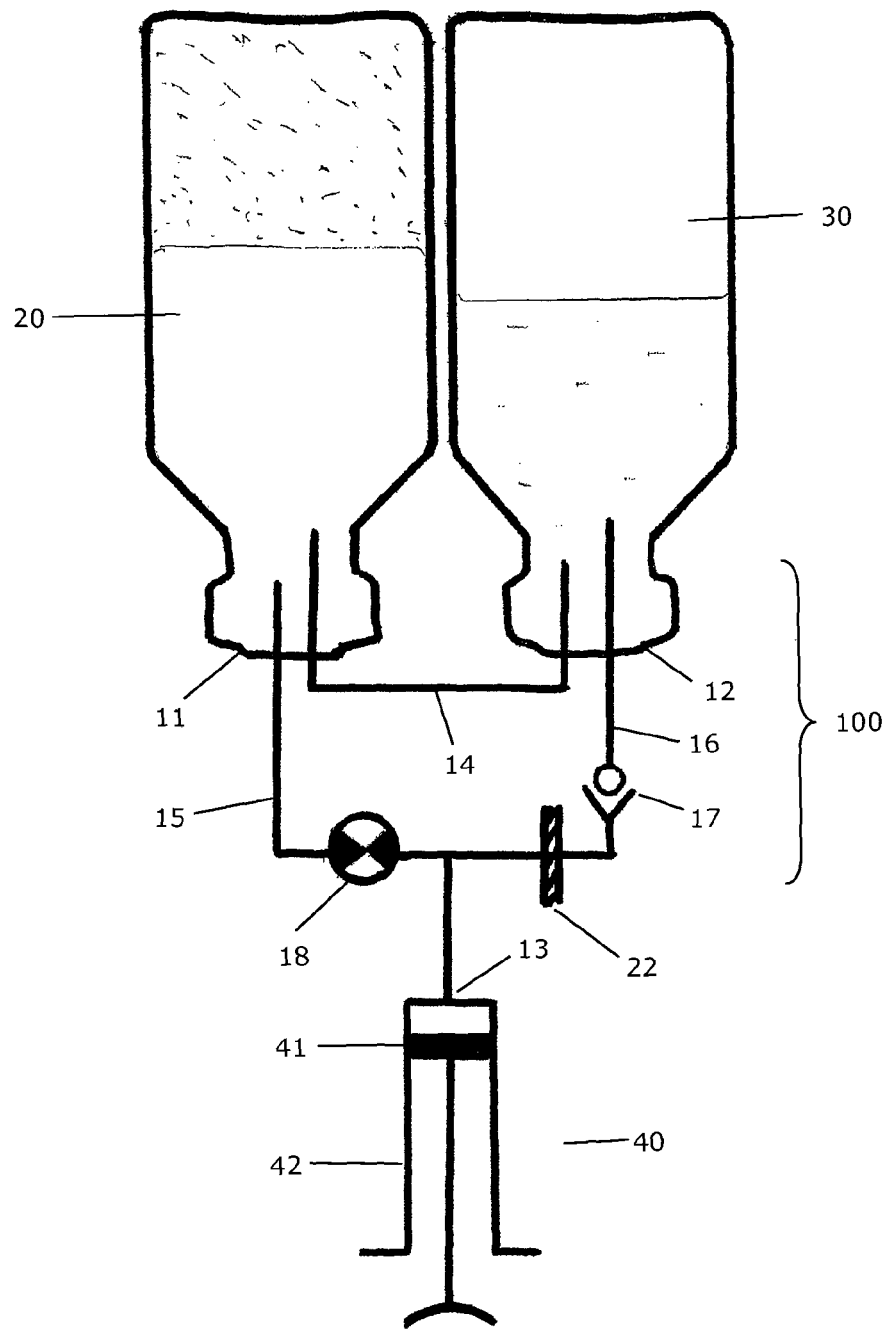

FIG. 7 is a schematic view of a seventh embodiment of a transfer system 100 according to the invention. The parts of the transfer system 100 of FIG. 7 which are identical to parts which have previously been described with reference to the preceding Figures will not be described in further detail here.

The transfer system 100 of FIG. 7 is very similar to the transfer systems 100 of FIGS. 1 and 6, and it is operated in a substantially identical manner. However, in FIG. 7 the filter 22 is arranged in the third channel 16. Accordingly, ambient air which has previously been sucked into the syringe 40 is filtered before it enters the second container 30, and the risk of contamination is thereby reduced.

Figure 8:
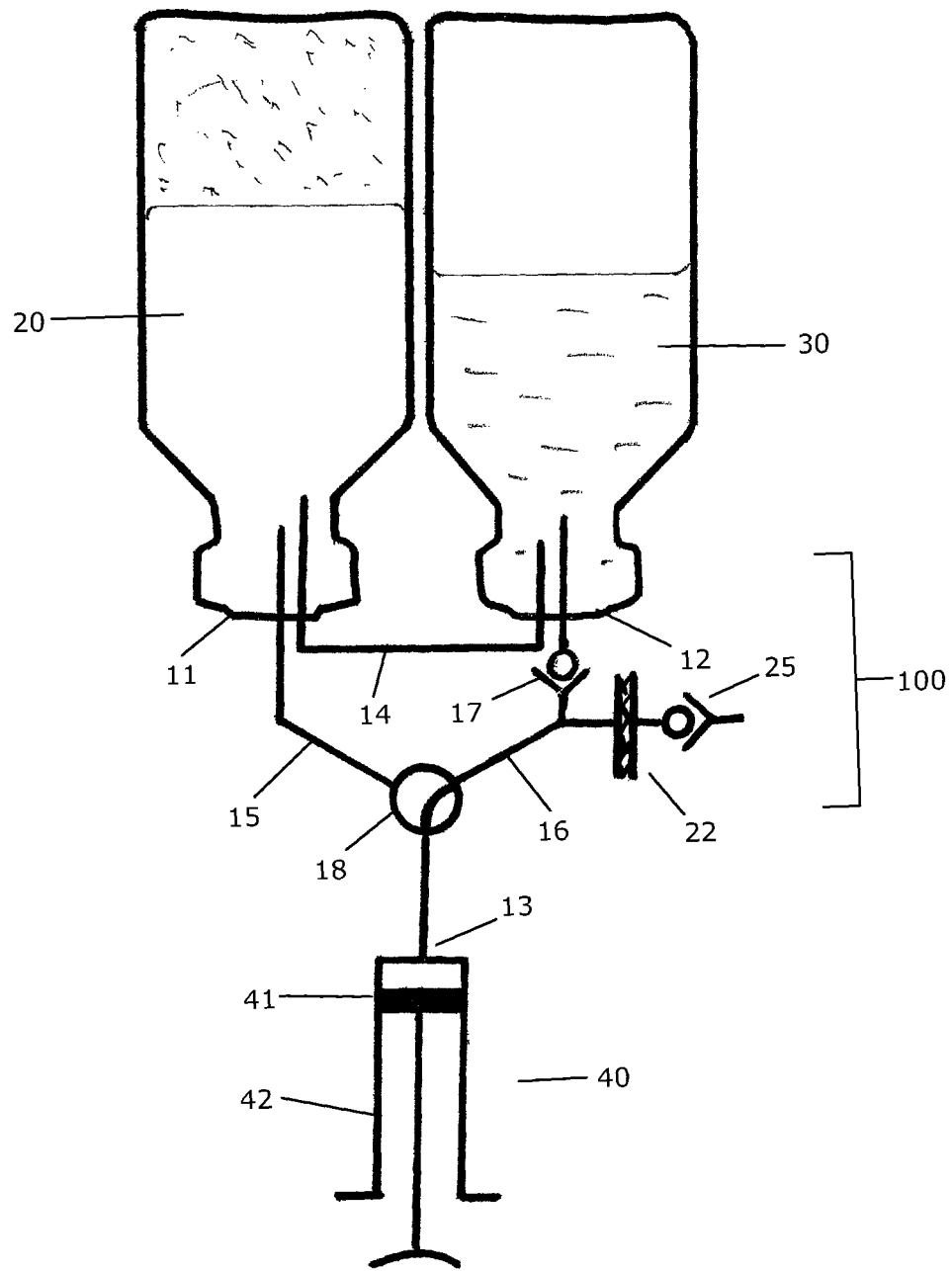

FIG. 8 is a schematic view of an eighth embodiment of a transfer system 100 according to the invention. The parts of the transfer system 100 of FIG. 8 which are identical to parts which have previously been described with reference to the preceding Figures will not be described in further detail here.

The transfer system 100 of FIG. 8 is very similar to the transfer system 100 of FIG. 6, and it is operated in a substantially identical manner. However, in the transfer system 100 of FIG. 8 the second flow control member 18 is of a kind which may form part of either the second channel 15 or the third channel 16. Accordingly, when the second flow control member 18 is operated to allow a fluid flow from the first container 20 to the syringe 40, a fluid connection between the syringe 40 and the second container 30, and between the syringe 40 and the filter 22 is automatically disrupted. Thereby it is prevented that ambient air is sucked into the syringe 40 via the filter 22 when the piston 41 is pulled back during transfer of the mixed material from the first container 20 to the syringe 40.

Figure 9:
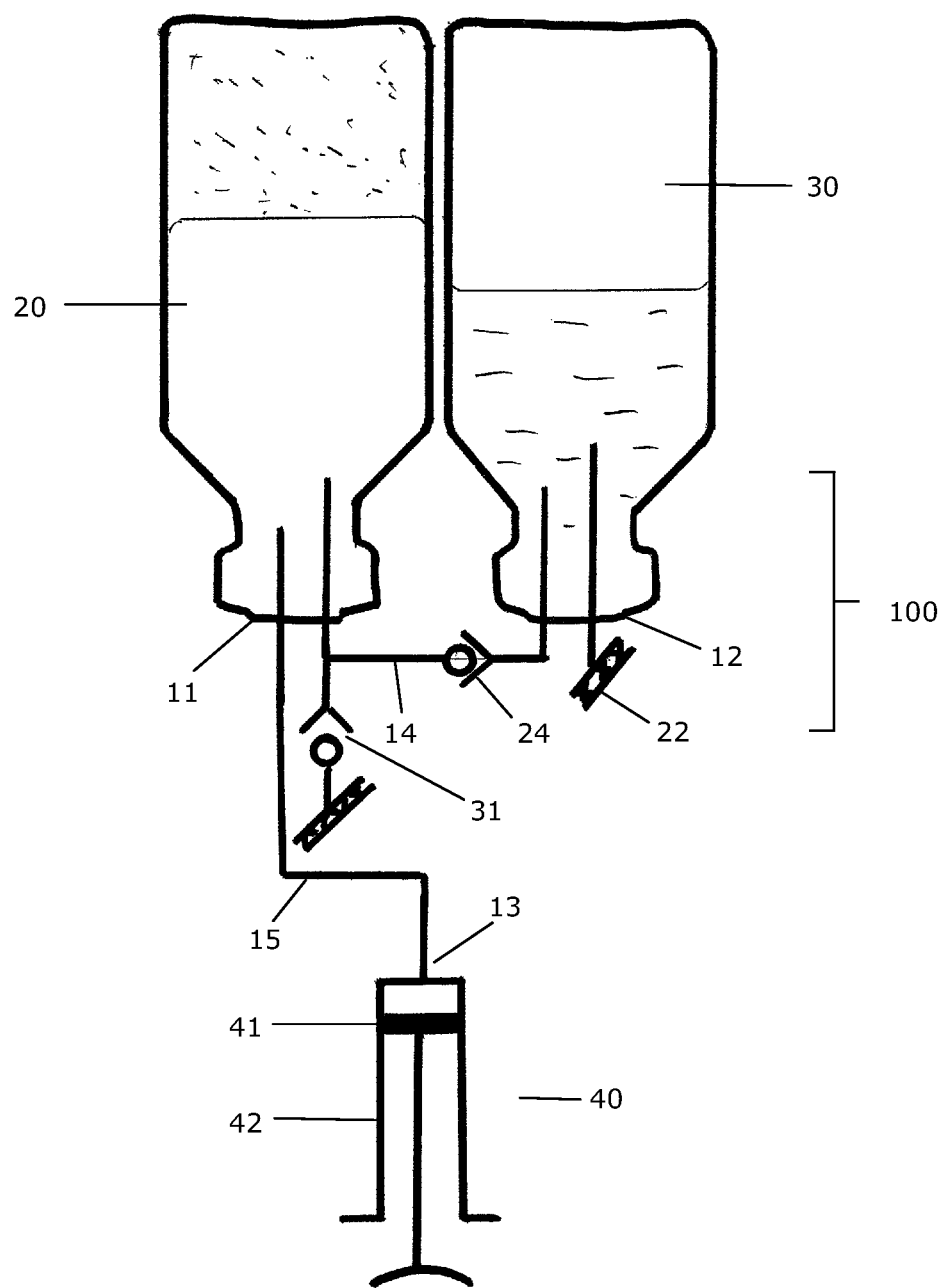

FIG. 9 is a schematic view of a ninth embodiment of a transfer system 100 according to the invention. The parts of the transfer system 100 of FIG. 9 which are identical to parts which have previously been described with reference to the preceding Figures will not be described in further detail here.

The transfer system 100 of FIG. 9 may be operated in the following manner. When it is desired to mix the contents of the first container 20 and the contents of the second container 30, it is initially ensured that the transfer system 100 is oriented as shown in FIG. 9, i.e. with the containers 20, 30 pointing in an upwards direction. The piston 41 of the syringe 40 is then pulled back, thereby causing valve 24 to open, and liquid is sucked from the second container 30 to the syringe 40 via channels 14, 15 and the first container 20. During this, ambient air enters the second container 30 via filter 22, thereby preventing a decrease of the pressure in the system. Since the transfer system 100 is oriented as described above, the liquid will not get into contact with the contents of the first container 20, since the contents of the first container 20 is stuck to the bottom of the first container 20.

When the liquid has been sucked into the syringe 40, the transfer system 100 is rotated in such a manner that the containers 20, 30 are pointing in a downwards direction. The piston 42 is then pushed in, and the liquid is thereby transferred from the syringe 40 to the first container 20, thereby causing the liquid to mix with the contents of the first container 20. Valve 24 is closed during this, thereby preventing that the liquid enters the second container 30. Air leaves the first container 20 via valve 31, thereby preventing an increase of the pressure in the system.

When the contents have been properly mixed, the transfer system 100 is once again rotated to the orientation shown in FIG. 9, and the piston 41 is once again pulled back, thereby sucking the mixed material into the syringe 40. Ambient air is sucked into the system via filter 22, thereby preventing a decrease of the pressure in the system.

Figure 12:
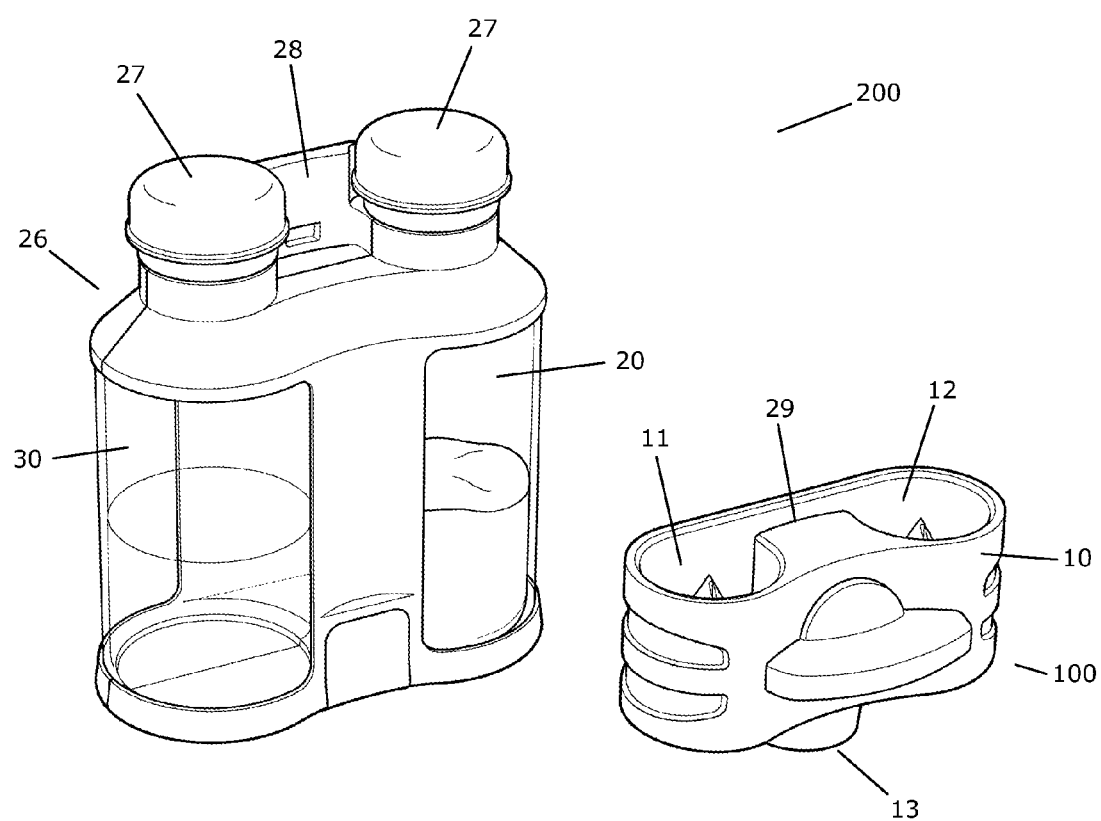
FIG. 12 is a perspective view of a drug mixing kit according to an embodiment of the invention in a disassembled state.

FIG. 12 is a perspective view of a drug mixing kit 200 according to an embodiment of the invention. The drug mixing kit 200 comprises a container unit 26 and a transfer unit 100, the container unit 26 and the transfer unit 100 being adapted to be coupled together to form the drug mixing kit 200.

The container unit 26 comprises a first container 20 containing first contents in the form of a dry drug, and a second container 30 containing second contents in the form of a diluent. The containers 20, 30 are fixed in the container unit 26, and it is thereby ensured that the first contents and the second contents match, e.g. in terms of amount and kind. Each of the containers 20, 30 is provided with a removable cap 27.

The transfer unit 100 comprises a first port 11 adapted to receive a first container 20, a second port 12 adapted to receive a second container 30, and a third port 13 adapted to be coupled to a syringe (not shown). The transfer unit 100 is further provided with a number of flow channels (not visible) connecting the ports 11, 12, 13 in such a manner that, when the transfer unit 100 and the container unit 26 are coupled together, the second contents is allowed to move from the second container 30 to the first container 20 in order to allow the first contents and the second contents to mix, and in such a manner that the mixed material is subsequently allowed to move to a syringe coupled to the third port 13.

When it is desired to mix the first contents and the second contents, the caps 27 are removed and the transfer unit 100 is positioned on top of the container unit 26 in such a manner that the first container 20 is received in the first port 11 and the second container 30 is received in the second port 12. The container unit 26 is provided with a wall part 28 which is arranged asymmetrically on the container unit 26. The transfer unit 100 is provided with a corresponding groove 29 adapted to accommodate the wall part 28. Thereby it is ensured that it is not possible to couple the container unit 26 and the transfer unit 100 in such a manner that the first port 11 is coupled to the second container 30 and the second port 12 to the first container 20. Accordingly, it is ensured that the fluid flows in the assembled drug mixing kit 200 are correct.

Figure 13:
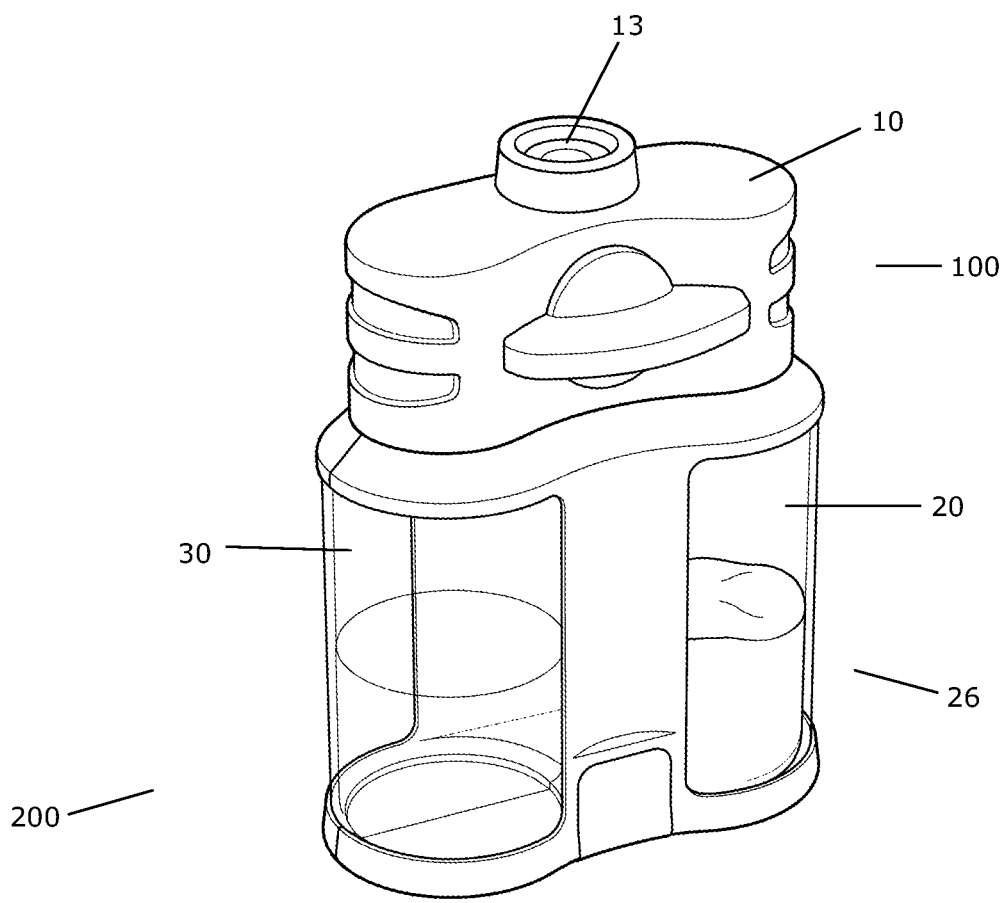
FIG. 13 is a perspective view of the drug mixing kit of FIG. 12 in an assembled state.

FIG. 13 is a perspective view of the drug mixing kit 200 of FIG. 12 in an assembled state.

In the above description of the exemplary embodiments, the different structures providing the desired relations between the different components just as the means providing the described functionality for the different components of a transfer system have been described to a degree to which the concept of the present invention will be apparent to the skilled reader. The detailed construction and specification for the different structures are considered the object of a normal design procedure performed by the skilled person along the lines set out in the present specification.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention claimed is:

1. A drug mixing kit comprising:
   a container unit comprising:
      a first container, said first container containing first contents, and
      a second container, said second container containing second contents to be mixed with the first contents to form a material, and
   a transfer unit comprising:
      first and second ports adapted to receive first and second containers of a container unit, and
      a third port for coupling to a syringe, the transfer unit further comprising a number of flow channels, at least some of the flow channels pair-wise interconnecting two of the first port, the second port and the third port,
      a flow control member enabling one-way fluid flow through a flow channel from the second port to the third port, and
      a flow control member enabling one-way fluid flow through a flow channel from the third port to the first port,
   wherein the container unit and the transfer unit are adapted to be coupled together to form a drug mixing kit.

2. A drug mixing kit according to claim 1, wherein the container unit and the transfer unit are shaped in such a manner that they can only be coupled together when being positioned at a predetermined mutual orientation.

* * * * *